United States Patent [19]

Niewöhner et al.

[11] Patent Number: 5,155,121
[45] Date of Patent: Oct. 13, 1992

[54] PHENYLSULPHONAMIDE SUBSTITUTED PYRIDINEALKENE- AND AMINOOXYALKANECARBOXYLIC ACID DERIVATIVES

[75] Inventors: Ulrich Niewöhner, Wermelskirchen; Ulrich E. Müller, Wuppertal; Elisabeth Perzborn, Wuppertal; Erwin Bischoff, Wuppertal; Hans-Georg Dellweg, Wuppertal, all of Fed. Rep. of Germany

[73] Assignee: Bayer Aktiengesellschaft, Leverkusen, Fed. Rep. of Germany

[21] Appl. No.: 739,747

[22] Filed: Aug. 2, 1991

[30] Foreign Application Priority Data

Aug. 16, 1990 [DE] Fed. Rep. of Germany ....... 4025818

[51] Int. Cl.$^5$ ................ C07D 213/55; C07D 213/57; A61K 31/44
[52] U.S. Cl. .................................... 514/357; 546/333
[58] Field of Search .......................... 546/333; 514/357

[56] References Cited

U.S. PATENT DOCUMENTS 3,838,120 9/1974 Zalay et al. .

FOREIGN PATENT DOCUMENTS 3817298 12/1988 Fed. Rep. of Germany .

OTHER PUBLICATIONS

Chemical Abstracts, vol. 111, Oct. 9, 1989, No. 15 "1--Pharmacology", p. 753.

Primary Examiner—Alan L. Rodman
Assistant Examiner—P. G. Spivack
Attorney, Agent, or Firm—Sprung Horn Kramer & Woods

[57] ABSTRACT

The compounds according to the invention can be prepared by reaction of the corresponding amines with sulphonic acid derivatives, or in the case of the aminooxy compounds by reaction of ketones with aminooxy compounds or alkylation of hydroxylamines, or in the case of the alkene compounds by reaction of ketones with phosphorusylides. The phenylsulphonamide substituted pyridinealkene- and -aminooxyalkenecarboxylic acid derivatives can be used for the treatment of thromboembolic disorders, ischaemias, arteriosclerosis, allergies and asthma.

11 Claims, No Drawings

PHENYLSULPHONAMIDE SUBSTITUTED PYRIDINEALKENE- AND AMINOOXYALKANECARBOXYLIC ACID DERIVATIVES

The invention relates to phenylsulphonamide substituted pyridinealkene- and -aminooxyalkanecarboxylic acid derivatives, to processes for their preparation and to their use in medicaments.

It is already known that pyridinealkenecarboxylic acids and pyridinemethyleneaminooxyalkanecarboxylic acids have a platelet aggregation-inhibitory action [cf. EP 221,601 and EP 135,316].

The invention relates to phenylsulphonamide-substituted pyridinealkene- and aminooxyalkanecarboxylic acid derivatives of the general formula (I)

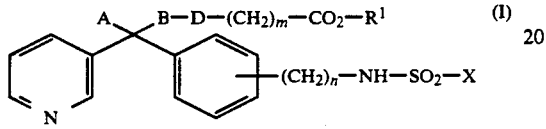

in which
- A—represents hydrogen,
- B—represents the —CH$_2$— group, or
- A and B together represent a radical of the formula =CN— or =N—,
- D—represents the —CH$_2$— group or in the case in which B denotes the radical of the formula =N—, then D represents oxygen,
- m—represents a number, 1, 2, 3, 4, 5, 6, 7, 8, 9 or 10,
- R$^1$—represents hydrogen or straight-chain or branched alkyl having up to 8 carbon atoms, or phenyl,
- n—represents a number 0 to 4,
- X—represents aryl having 6 to 10 carbon atoms or an unsaturated 5- to 7-membered heterocycle having up to 3 heteroatoms from the series comprising oxygen, sulphur or nitrogen, which are optionally monosubstituted to trisubstituted by identical or different substituents from the series comprising halogen, cyano, phenoxy, trifluoromethoxy and straight-chain or branched alkyl having up to 8 carbon atoms which, in turn, can be monosubstituted to trisubstituted by identical or different halogen substituents and their salts.

The substances according to the invention surprisingly show a good thromboxane synthase-inhibiting and thromboxane antagonist action and can be used for the treatment of thromboembolic disorders.

In the context of the present invention, physiologically acceptable salts are preferred. Physiologically acceptable salts of the phenylsulphonamide-substituted pyridinealkene- and aminoalkanecarboxylic acid derivatives can be salts of the substances according to the invention with bases. In general, salts with inorganic or organic bases may be mentioned here.

Salts in the context of the present invention are additionally salts of the univalent metals such as alkali metals and the ammonium salts. Sodium, potassium and ammonium salts and triethylammonnium salt are preferred.

The compounds according to the invention exist in stereoisomeric forms which behave as image and mirror image (enantiomers: A=H, B=CH$_2$, D=CH$_2$). The invention relates both to the antipodes and to the racemic modifications. The racemic modifications can be resolved into the stereoisomerically homogeneous constituents in a known manner (cf. E. L. Eliel, Stereochemistry of Carbon Compounds, McGraw Hill, 1962).

Additionally, in the case in which A and B together represent the radicals =CH— or =N— and D, corresponding to the abovementioned meaning, either represents the —CH$_2$— group or oxygen, isomeric forms with respect to the position of the substituents on the double bond can occur. The invention relates both to the individual isomers and to their mixtures.

Preferred compounds of the general formula (I) are those in which
- A—represents hydrogen,
- B—represents the —CH$_2$ group, or
- A and B together represent a radical of the formula =CH— or =N—,
- D—represents the —CH$_2$— group or in the case in which B with A denotes the radical of the formula =N—, then D represents oxygen,
- m—represents a number 1, 2, 3, 4, 5, 6, 7 or 8,
- R$^1$—represents hydrogen or straight-chain or branched alkyl having up to 6 carbon atoms,
- n—represents a number 0 or 1,
- X—represents phenyl or pyridyl which are optionally monosubstituted to trisubstituted by identical or different substituents from the series comprising fluorine, chlorine, bromine, cyano, phenoxy, trifluoromethyl, trifluoromethoxy and straight-chain or branched alkyl having up to 6 carbon atoms and their salts.

Particularly preferred compounds of the general formula (I) are those in which
- A—represents hydrogen,
- B—represents the —CH$_2$— group, or
- A and B together represent a radical of the formula =CH— or =N—,
- D—represents the —CH$_2$— group or in the case in which B with A denotes the radical of the formula =N—, then D represents oxygen,
- m—represents a number 1, 2, 3, 4, 5 or 6,
- R$^1$—represents hydrogen or straight-chain or branched alkyl having up to 4 carbon atoms,
- n—represents a number 0 or 1,
- X—represents phenyl or pyridyl which are optionally monosubstituted to trisubstituted by identical or different substituents from the series comprising fluorine, chlorine, cyano, phenoxy, trifluoromethyl, trifluoromethoxy and straight-chain or branched alkyl having up to 4 carbon atoms and their salts.

In addition, a process for the preparation of compounds of the general formula (I) according to the invention

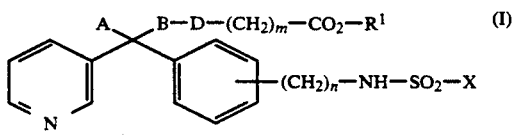

in which
A, B, D, m, R$^1$, n and X have the abovementioned meaning, has been found, which is characterised in that

[A] in the case in which A and B together represent the radical of the formula =N— and D denotes oxygen, compounds of the general formula (II)

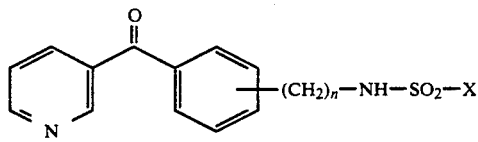

in which n and X have the abovementioned meaning, are either reacted directly with compounds of the general formula (III)

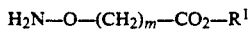

in which
m and R¹ have the abovementioned meaning,
if appropriate in the form of their salts, in inert solvents, if appropriate in the presence of a base,
or are first reacted with hydroxylamine by a customary method to give the corresponding oximes of the general formula (IV)

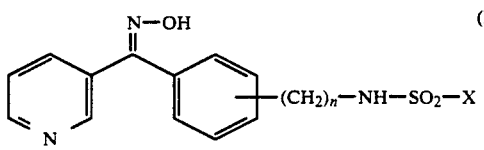

in which
n and X have the abovementioned meaning,
and the oximes are then reacted with carboxylic acid derivatives of the general formula (V)

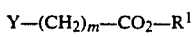

in which
m and R¹ have the abovementioned meaning and
Y—represents a typical leaving group, in inert solvents, in the presence of a base, or
[B] in the case in which A and B together represent a radical of the formula =CH— and D denotes the —CH₂— group,
the compounds of the general formula (II) are reacted in inert solvents and in the presence of a base with ylide compounds of the general formula (VI)

in which
m and R¹ have the abovementioned meaning and
Z—represents a halogen atom, preferably bromine, or
[C] compounds of the general formula (VII)

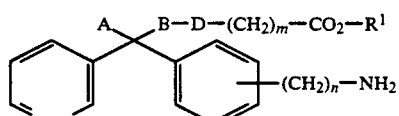

in which
A, B, D, n, m and R¹ have the abovementioned meaning, are sulphonated using compounds of the general formula (VIII)

in which
X and Y have the abovementioned meaning,
and in the case in which A represents hydrogen and B and D represent the —CH₂— group, a catalytic reduction is added according to a customary method,
and in all processes [A], [B] and [C], in the case of the acids (R¹=H) the esters are hydrolysed according to a customary method.

The processes according to the invention can be illustrated by the following reaction scheme:

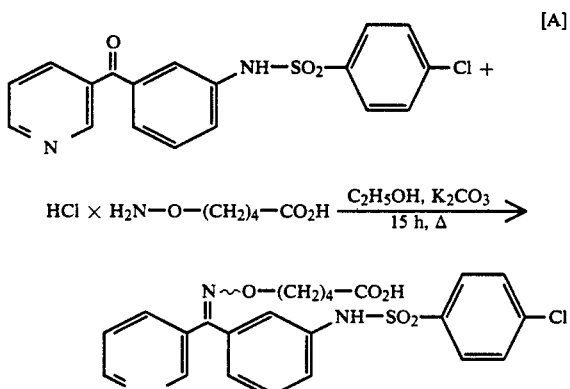

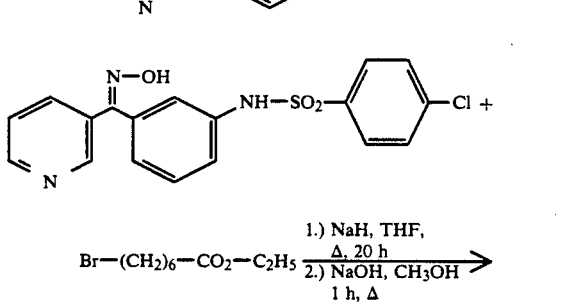

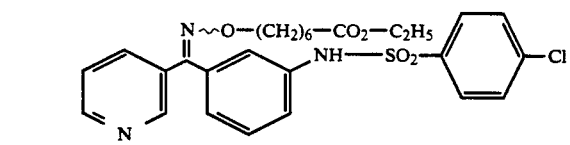

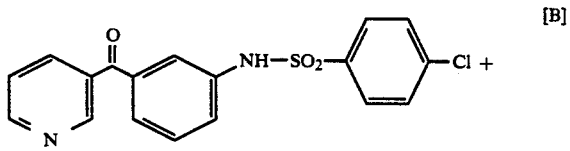

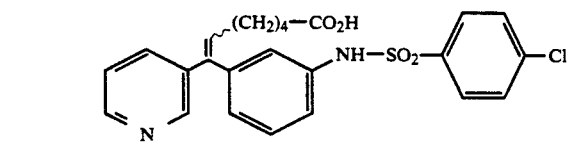

-continued

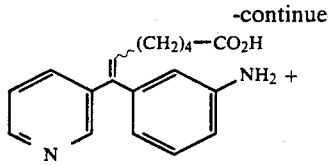

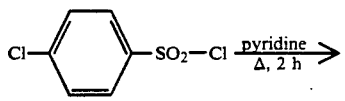

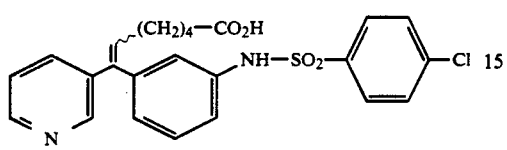

Basically, the customary organic solvents which do not change under the reaction conditions can be employed as solvents for processes [A], [B] and [C]. These preferably include ethers such as diethyl ether, dioxane, tetrahydrofuran, glycol dimethyl ether, or hydrocarbons such as benzene, toluene, xylene, hexane, cyclohexane or mineral oil fractions, or halogenohydrocarbons such as dichloromethane, trichloromethane, tetrachloromethane, dichloroethylene, trichloroethylene or chlorobenzene, or ethyl acetate, triethylamine, pyridine, dimethyl sulphoxide, dimethylformamide, hexamethylphosphoric triamide, acetonitrile, acetone or nitromethane. It is also possible to use mixtures of the solvents mentioned. Depending on the individual reaction steps, ethanol, tetrahydrofuran, pyridine and tert. butanol are particularly preferred.

Suitable bases for processes [A] and [B] are, for example, alkali metal and alkaline earth metal carbonates such as potassium carbonate, sodium carbonate, calcium carbonate, alkali metal and alkaline earth metal hydroxides such as sodium hydroxide, potassium hydroxide, calcium hydroxide, alkali metal and alkaline earth metal hydrides such as sodium hydride or calcium hydride, organolithium compounds such as butyllithium or phenyllithium, alkali metal alkoxides such as sodium methoxide, sodium ethoxide or potassium tert. butoxide or organic bases such as, for example, triethylamine or pyridine.

The reactions for processes [A] and [B] can be carried out at normal or elevated pressure (for example 1.0 to 5 bar), preferably at normal pressure.

The sulphonation [C] is in general carried out in a temperature range from −80° C. to +150° C., preferably from 0° C. to +80° C.

The sulphonation is in general carried out at normal pressure. However, it is also possible to carry out the process at elevated pressure or at reduced pressure (for example in a range from 0.5 to 5 bar).

In general, 1 to 3 mol, preferably 1 to 2 mol, particularly preferably 1 mol of sulphonyl compound (VIII) is employed relative to 1 mol of the amine (VII).

Acid-binding agents which can be employed for the sulphonation are alkali metal or alkaline earth metal carbonates such as sodium carbonate, potassium carbonate, alkali metal or alkaline earth metal hydroxides such as, for example, sodium hydroxide or potassium hydroxide, or organic bases such as pyridine, triethylamine, N-methylpyridine, or bicyclic amidines such as 1,5-diazabicyclo-[3.4.0]non-5-ene (DBN) or 1,5-diazabicyclo[5.4.0]undec5-ene (DBU). Potassium carbonate is preferred.

The acid-binding agents are in general employed in an amount of 0.5 to 3 mol, preferably of 1 to 1.5 mol, relative to the compounds of the general formula (VIII).

Reduction of the double bond by hydrogenation is in general carried out using hydrogen in the presence of a catalyst such as, for example, platinum or platinum oxides, rhodium, ruthenium, chlorotris(triphenylphosphine)rhodium, or palladium on animal charcoal, preferably using palladium on animal charcoal in a temperature range from 0° C. to +150° C., preferably from +25° C. to 100° C.

Suitable solvents for the hydrogenation are protic solvents such as, for example, methanol, ethanol and/or aprotic solvents such as, for example, tetrahydrofuran, toluene, dimethylformamide, methylene chloride or dioxane.

The hydrogenation is carried out at a pressure of 1 to 300 atm, preferably at 1 to 20 atm.

The amount of catalyst employed is 0.5 to 5, preferably 1 to 1.5 mol per cent relative to the compound of the general formula (I, A and B=−CH—, D=—CH$_2$).

Hydrolysis of the carboxylic acid esters is carried out by customary methods, by treating the esters with customary bases in solvents, it being possible to convert the initially formed salts into the free carboxylic acids by treating with acid.

Suitable bases for the hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium ethoxide, potassium methoxide or potassium tert. butoxide. Sodium hydroxide or potassium hydroxide are particularly preferably employed.

Suitable solvents for the hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. Alcohols such as methanol, ethanol, propanol or isopropanol are particularly preferably used. It is also possible to employ mixtures of the solvents mentioned.

The hydrolysis is in general carried out in a temperature range from 0° C. to +100° C., preferably from +20° C. to +80° C.

In general, the hydrolysis is carried out at normal pressure. However, it is also possible to work at reduced pressure or at elevated pressure (for example from 0.5 to 5 bar).

When carrying out the hydrolysis, the base is in general employed in an amount from 1 to 3 mol, preferably from 1 to 1.5 mol relative to 1 mol of the ester. Molar amounts of the reactants are particularly preferably used.

A suitable typical leaving group Y in the compounds of the general formulae (V) and (VIII) is Cl, Br, I, —O-SO$_2$CH$_3$ and —OSO$_2$—C$_6$H$_4$—p—CH$_3$.

The compounds of the general formula (III) are known per se [cf. Tetrahedron 23, (1967), 4441–4447) or can be prepared by the processes described therein.

The carboxylic acid derivatives of the general formula (V) are also known [cf. Beilstein 3, 5; Fieser 1, 247; 2, 129; 3, 95; 5, 213].

The ylide compounds of the general formula (VI) [cf. J. Med. Chem. 28 (1985), 3, 287] and the sulphonic acids and their activated derivatives of the general formula (VIII) [cf. Houben-Weyl's, "Methoden der organischen Chemie (Methods of Organic Chemistry), Volume IX, p. 407 et seq.] are known or can be prepared by the methods mentioned.

The compounds of the general formula (II) are new and can be prepared by reacting the sulphonic acid derivatives of the general formula (VIII) mentioned above with amines of the general formula (IX)

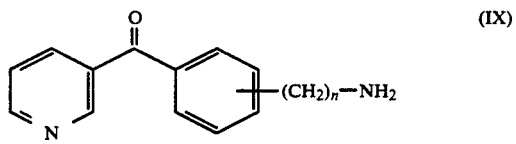

in which n has the abovementioned meaning, by the conditions indicated under process [C].

The compounds of the general formula (IX) are known in some cases (n=0) [cf. J. Med. Chem. 24 (1981) 12, 1499] or can be prepared by the process described therein;

in the case in which n denotes the number 1, the compounds can be prepared by initially oxidising the hydroxyl group to the carbonyl group in analogy to processes known in the literature in the corresponding hydroxy-cyano compounds (X)

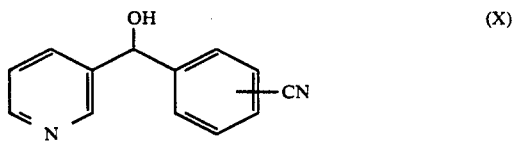

by a customary method and then reducing the cyano group [for this cf. J. Med. Chem. 1986, 29, 1461; J. Chem. Soc. Perkin Trans 1, (1972), 1655; J. Org. Chem. 1978, 43, 4537,; Rylander "Catalytic Hydrogenation over Platinium Metals", Academ. Press., Inc., New York (1967)].

The compounds of the general formula (X) are known [cf. EP 221,601 A1].

The compounds of the general formula (IV) are also new and can be prepared by the abovementioned method.

The compounds of the general formula (VII) are new and can be prepared by reducing compounds of the general formula (XI)

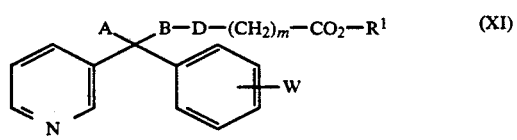

in which

A, B, D, m and $R^1$ have the abovementioned meaning and

W in the case in which n in the compounds of the general formula (VII) represents the number 0 denotes nitro and in the case in which n represents the number 1 denotes cyano, by a customary method.

The reduction proceeds in analogy to processes known from the literature [cf. EP 337,640; J. March "Advanced Organic Chemistry", p. 1125 (2nd Edition); Rabinowitz in Rappoport, "The Chemistry of the Cyano Group", p. 307-340; Interscience Publishers, New York (1970)].

The compounds of the general formula (XI) are known [cf. EP 221,601, 135,316].

The compounds according to the invention, their salts and isomers can be employed as active compounds in medicaments. The substances have a platelet aggregation-inhibiting and thromboxane $A_2$-antagonist action and inhibit the thromboxane synthase in isolated platelets. They can be employed for the treatment of thromboembolic disorders and ischaemias such as myocardial infarct, stroke, transitory and ischaemic attacks, angina pectoris, peripheral circulatory disorders, prevention of restenoses such as after thrombolysis therapy, percutaneous transluminal angioplasties (PTA), percutaneous transluminal coronary angioplasties (PTCA), by-pass and for the treatment of arteriosclerosis, asthma and allergies.

Blood from healthy donors of both sexes was used for the determination of the platelet aggregation-inhibiting action. As an anticoagulant, 9 parts of blood were admixed to one part of 3.8% strength aqueous sodium citrate solution. Platelet-rich citrate plasma (PRP)[1] is obtained from this blood by means of centrifugation (Jürgens/Beller, Klinische Methoden der Blutgerinnungsanalyse (Clinical Methods of Blood Coagulation Analysis); Thieme Verlag, Stuttgart, 1959).

For these investigations, 0.8 ml of (PRP)[1] and 0.1 ml of the active compound solution were preincubated in a water bath at 37° C. The platelet aggregation was then determined by the turbidometric method (Born, G.V.R., J. Physiol. (London), 162, 67, 1962) in an aggregometer at 37° C. (Therapeutische Berichte 47, 80-86, 1975). To this end, 0.1 ml of collagen, an aggregation-inducing agent, was added to the preincubated sample. The change in the optical density in the sample of the (PRP) was recorded during a period of 6 minutes and the result was determined after 6 minutes. To do this, the percentage inhibition was calculated compared to the control.

The range of the minimum effective concentration was given as the threshold concentration.

| Example No. | TAI threshold concentration (µg/ml) |
|---|---|
| I | 0.3-1.0 |
| II | 1-3 |
| XII | 1-3 |
| XIII | >10 |
| XV | 3-10 |
| XXVI | 0.1-0.3 |

Measurement of the thromboxane synthase in washed human platelets

I. Preparation of platelet suspensions

Blood from healthy donors is taken up in EDTA (1% in 0.9% NaCl, 9+1) and centrifuged at 1000 rpm (150 g) for 20 min. The platelet-rich plasma (PRP)[2] is taken off and in each case 10 ml are centrifuged at 2500 rpm for 20 min. The platelet-rich plasma[2] is decanted off. The platelets which remain are suspended in 5 ml of resuspension buffer (0.15 M TRIS / 0.9% NaCl / 77 mmol EDTA, 8:91:1; adjusted to pH 7.4 with 1 N HCl), centrifuged for 20 min at 2500 rpm and suspended in 1 ml of resuspension buffer. The platelet count is adjusted to $3 \times 10^5/\mu l$.

2. Measurement of the thromboxane synthase 1 ml of the platelet suspension and 0.01 ml of the test preparation in 10% DMSO- are incubated at 37° C. for 2 min. 0.1 ml of $^3$H-arachidonic acid from Amersham Buchler GmbH and Co. KG ($6.6 \times 10^{-5}$ mol/l) having a specific activity of 140 MBq/mmol are added to this and the mixture is incubated at 37° C. for a further 10 min. After the reaction, the mixture is acidified using about 0.02 ml of 0.5 N citric acid and immediately extracted 3 times with 1 ml of ethyl acetate each time. The supernatants are collected in 10 ml glass tubes and the ethyl acetate is blown off at 25° C. under $N_2$. The residue is taken up in 50 $\mu l$ of MeOH/ $CHCl_3$ (1:1) and applied to TLC glass plates (silica gel 60, F254, $20 \times 20$ cm, Merck).

Separation is carried out in an eluent mixture of $CHCl_3$/MeOH/glacial acetic acid/$H_2O$ (80:8:1:0.8). The distribution of the radioactivity is detected in a Ramona-Ls TLC scanner from Raytest and quantitatively evaluated using an integration program.

The concentration of the test substances which leads to a 50% inhibition of thromboxane formation compared to the control is determined.

Inhibition of thromboxane synthase in washed platelets from human blood.

| Example No. | $IC_{50}$ mol/l |
|---|---|
| 1 | $0.5-1 \times 10^{-9}$ |
| 5 | $0.5-1 \times 10^{-9}$ |

Thromboxane receptor binding test on human platelet membranes a) Membrane preparation The blood taken the previous evening according to standard methods was centrifuged at 2800 rpm for 10 min at 10° C. in the morning. 10 $\mu M$ indomethacin was added to the buffy coat formed during the course of this as a layer between the platelet-poor plasma and the erythrocytes. Platelet membranes were prepared from the buffy coat by a method which was described by Barber and Jamieson (cf. Barber, A. J., Manieson, G. A.: Isolation and characterization of plasma membranes form human blood platelets, J. Biol. Chem. 245, 6357-6365, 1970). As the most important step here, platelets are loaded with glycerol and lysed by osmotric shock.

The washed membranes obtained in this way were resuspended in tris-NaCl-glucose buffer (50 mM tris, 100 mM NaCl, 5 mM glucose, pH 7.4), rapidly frozen in dry ice and stored at $-70°$ C.

b) Displacement studies

For the displacement studies, 100 $\mu g$ of membrane protein and about 5 nM $^3$H-(3R)-3-(4-fluorophenylsulphonamido)-9-(2-carboxyethyl)-1,2,3,4-tetrahydro-4a,4$\beta$-carbazole [for preparation cf. DOS (German Published Specification) 3,631,824; radioactive labelling is carried out by a method known from the literature] were incubated in a total volume of 1 ml of tris-NaCl-glucose buffer. Increasing concentrations of the displacing unlabelled compounds according to the invention dissolved in DMSO were added to the mixture (final concentration, 0.5% DMSO, relative to the assay volume).

The substance concentration $IC_{50}$ which is needed to displace 50% of the specific binding was determined with the aid of a logit-log plot according to HILL. The inhibition constant $K_I$ was determined from the $IC_{50}$ and the dissociation constants $K_D$ (determined by Scatchard analysis).

The present invention also includes pharmaceutical preparations which contain one or more compounds of the general formula (I) or which consist of one or more active compounds of the formula (I) in addition to inert, non-toxic, pharmaceutically suitable auxiliaries and excipients, and processes for the production of these preparations.

The active compounds of the formula (I) should be present in these preparations in a concentration of 0.1 to 99.5% by weight, preferably of 0.5 to 95% by weight of the total mixture.

In addition to the active compounds of the formula (I), the pharmaceutical preparations may also contain other pharmaceutical active compounds.

The abovementioned pharmaceutical preparations can be prepared in a customary manner according to known methods, for example with the auxiliary(ies) or excipient(s).

In general, it has proved advantageous to administer the active compound(s) of the formula (I) in total amounts from about 0.03 to about 30 mg/kg, preferably up to about 5 mg/kg of body weight every 24 hours, if appropriate in the form of several individual doses, to achieve the desired result.

An individual dose contains the active compound(s) preferably in amounts from 0.01 to about 10, particularly preferably 0.1 to 1.0 mg/kg of body weight.

If appropriate, however, it may be advantageous to depart from the amounts mentioned, in particular depending on the nature and the body weight of the subject to be treated, on individual behaviour to the medicament, the nature and severity of the disorder, the manner of preparation and administration, and the point or interval at which administration takes place.

STARTING COMPOUNDS

EXAMPLE 1

3-(4-Chlorophenylsulphonamido)-phenyl 3-pyridinyl ketone

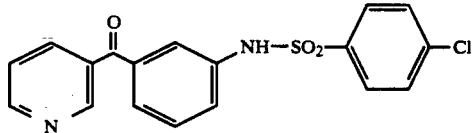

3.96 g (20 mmol) of 3-aminophenyl 3-pyridinyl ketone and 4.22 g (20 mmol) of 4-chlorobenzenesulphonyl chloride are refluxed in 40 ml of THF for 24 h. After cooling to room temperature, the solvent is evaporated in vacuo and the residue is dissolved in 100 ml of methylene chloride and 100 ml of saturated sodium hydrogen carbonate solution. The methylene chloride phase is separated off, dried using sodium sulphate and evaporated. The residue is chromatographed on silica gel using methylene chloride/ acetone 10:1 as the eluent.

Yield: 4.98 g (66.8.% of theory)

M.p.: 140°-142° C. (after chromatography, not recrystallised)

$R_f = 0.52$ ($CH_2Cl_2$/MeOH 10:1)

The compounds shown in Table 2 were prepared in an analogous manner to that described in Example 1.

TABLE 1

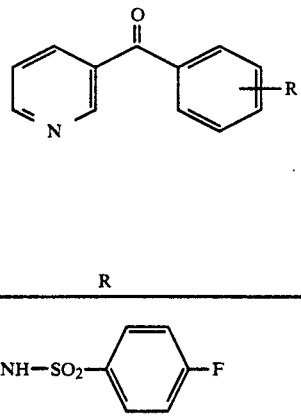

| Ex. No. | R | M.p. (after chromatography, not recrystallised) |
|---|---|---|
| 2 | 3-NH—SO₂—⟨C₆H₄⟩—F | 132° C. |
| 3 | 3-NH—SO₂—⟨C₆H₃⟩(Cl)(Cl) | 195° C. |
| 4 | 3-NH—SO₂—⟨C₆H₄⟩—OCF₃ | 69° C. |
| 5 | 3-NH—SO₂—⟨C₆H₄⟩—CF₃ | 173° C. |
| 6 | 3-NH—SO₂—⟨C₆H₄⟩—O—⟨C₆H₅⟩ | 58° C. |
| 7 | 3-NH—SO₂—⟨C₆H₄⟩—CN | 75° C. |
| 8 | 3-NH—SO₂—⟨C₆H₄⟩—C(CH₃)₃ | 177° C. |
| 9 | 2-NH—SO₂—⟨C₆H₄⟩—Cl | — |
| 10 | 4-NH—SO₂—⟨C₆H₄⟩—Cl | 177–179° C. |

EXAMPLE 11
3-(4-Chlorophenylsulphonamido)-phenyl 3-pyridinyl ketone oxime

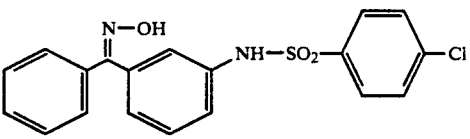

7.45 g (20 mmol) of the compound from Example 1, 2.08 g (30 mmol) of hydoxylammonium chloride and 4.14 g (30 mmol) of potassium carbonate are refluxed in 20 ml of ethanol for 15 h. After cooling to room temperature, the mixture is evaporated and the residue is stirred in 50 ml of water for 3 h (after this time no oily residues, but only crystalline residues, were still undissolved). The precipitate was filtered off, washed with water and recrystallised from methanol by addition of water. Yield: 5.71 g (73.7% of theory) M.p.: 170° C.

EXAMPLE 12
3-Cyanophenyl-3-pyridinyl-methanol

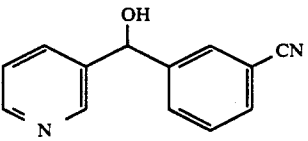

52.8 ml of 2.5 molar butyllithium solution (0.132 mol) in n-hexane are cooled to −78° C. under argon in a mixture of 66 ml of abs. THF and 66 ml of abs. diethyl ether. 17.38 g (0.11 mol) of 3-bromopyridine in 132 ml of abs. diethyl ether are added dropwise to this in the course of 90 min. and the mixture is subsequently stirred for 10 min. 14.5 g (0.11 mol) of 3-cyanobenzaldehyde in 275 ml of abs. diethyl ether and 44 ml of abs. THF are added dropwise to this solution. It is slowly allowed to come to room temperature and stirred overnight at room temperature. It is then stirred into 1100 ml of ice water, extracted twice using 550 ether each time and the combined organic phases are washed by shaking with satd. NaCl solution. After drying over Na₂SO₄, the organic phase is evaporated and the residue is dried in a high vacuum.
Yield: 15.7 g (68% of theory)
M.p.: 132°–135° C.

EXAMPLE 13
3-Cyanophenyl 3-pyridinyl ketone

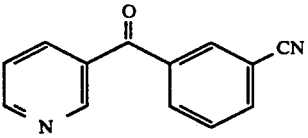

3.3 ml of oxalyl chloride are initially introduced into 75 ml of abs. CH₂Cl₂ at −60° C. under argon. First 6 ml of abs. DMSO in 7.5 ml of abs. CH₂Cl₂, then 6.3 g (30 mmol) of the compound from Example 12 in 75 ml of abs. CH₂Cl₂ are added dropwise to this. The mixture is subsequently stirred at −60° C. for 15 min, and then 22.5 ml of triethylamine are added dropwise. The mixture is allowed to come to room temperature and is subsequently stirred for 3 h, and then 30 ml of water are added. The methylene chloride is evaporated in a water-jet vacuum and the aqueous phase is shaken twice with ethyl acetate. The combined ethyl acetate phases are washed with water, dried over $Na_2SO_4$ and evaporated. The residue is a product which is clean by TLC.

Yield: 6.15 g (98.6% of theory)
$R_f$=0.72 ($CH_2Cl_2$/MeOH 10:1)

EXAMPLE 14

3-Aminomethylphenyl 3-pyridinyl ketone

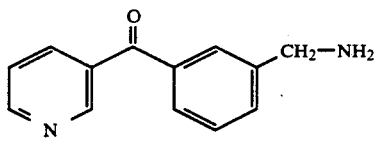

4.16 g (20 mmol) of the compound from Example 13 are hydrogenated at normal pressure for 6 h at 20° C. in 20 ml of aqueous ammonia solution in the presence of 1 g of RaNi. The aqueous phase is rendered acidic by addition of conc. HCl and 3 times with 30 ml of THF each time, to which 5 ml of ethyl acetate is admixed and extracted for better phase separation. The combined organic phases are dried over sodium sulphate and evaporated. The residue is chromatographed on silica gel using $CH_2Cl_2$/MeOH 3:1 as the eluent.

Yield: 1.145 g (27% of theory)
$R_f$=0.46 ($CH_2Cl_2$/MeOH 3:1)

EXAMPLE 15

3-(4-Chlorophenylsulphonamidomethyl)phenyl 3-pyridinyl ketone

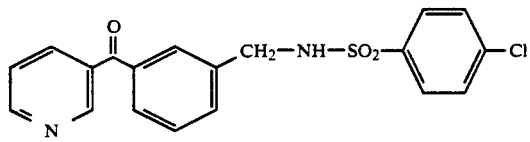

The compound from Example 14 and 4-chlorophenylsulphonyl chloride are reacted analogously to Example 1.
Yield: 54%
$R_f$=0.54 ($CH_2Cl_2$/MeOH 10:1)
M.p.: 78°–79° C. (after chromatography, not recrystallised)

EXAMPLE 16

(E/Z)-7-(3-Aminophenyl)-7-(3-pyridinyl)-6-hexene-carboxylic acid

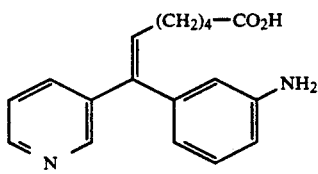

26.4 g (81 mmol) of (E/Z)-7-(3-nitrophenyl)-7-(3-pyridinyl)-6-hexene-carboxylic acid [cf. J. Med. Chem. 1985, 28, 287–294] and 52.23 g (300 mmol) of $Na_2SO_4$ are heated to reflux for 3 h in 162 ml of glycol monomethyl ether and 162 ml of water. The mixture is cooled to 60° C. and 121.5 ml of conc. HCl are added dropwise at this temperature. The mixture is then refluxed for 15 min, cooled and poured into 800 ml of ice-water. The acidic solution is adjusted to pH 5.5 using saturated $Na_2CO_3$ solution and extracted 3 times using ethyl acetate. After drying over $Na_2SO_4$, the combined organic phases are evaporated. The residue is taken up in 10% strength NaOH and shaken twice with $CH_2Cl_2$. The NaOH phase is adjusted to pH 5.5 using conc. HCl and shaken 3 times with ethyl acetate. After drying over $Na_2SO_4$, the organic phase is evaporated and the clean product is obtained as E/Z isomers in the ratio of about 2:3 (E/Z relative to the pyridine ring).

Yield: 17.04 g (7.1.% of theory)
$R_f$=0.36 ($CH_2Cl_2$/MeOH 10:1)

The amines summarised in Table 2 are prepared analogously:

TABLE 2

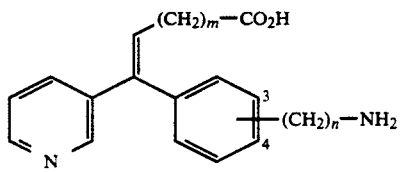

| Ex. No. | Position | m | n | $R_f$ values* |
|---|---|---|---|---|
| 17 | 3 | 3 | 0 | 0.26 |
| 18 | 3 | 5 | 0 | 0.34 |
| 19 | 3 | 6 | 0 | 0.36 |
| 20 | 4 | 4 | 0 | 0.32 |
| 21 | 3 | 4 | 1 | 0.35 |

*Eluent mixture: $CH_2Cl_2$/MeOH 10:1

PERPETRATION EXAMPLES (GENERAL FORMULA I)

EXAMPLE I (E/Z)-5-[[[3-Pyridinyl-3-(4-chlorophenylsulphonamido)phenyl]methylene]iminooxy]pentanecarboxylic acid

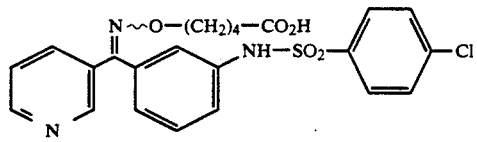

3.4 g (10 mmol) of the compound from Example 1 and 1.68 g (10 mmol) of 5-aminooxy-pentanecarboxylic acid hydrochloride are refluxed in 20 ml of abs. ethanol for 15 h together with 4.14 g (30 mmol) of potassium carbonate. After cooling to room temperature, the mixture is poured into 50 ml of water and shaken twice with methylene chloride. The aqueous phase is adjusted to pH 5 using 1 N HCl and shaken 3 times with THF, to which some ethyl acetate is added for better phase separation. After drying over sodium sulphate, the mixture is evaporated and dried in a high vacuum. The compound consists of an E/Z mixture, but contains no other impurities.

Yield: 3.95 g (81% of theory)
M.p.: 75° C. (not recrystallised)

The compounds shown in Table 3 were prepared in an analogous manner to that described in Example I:

TABLE 3

N~O—(CH₂)ₘ—CO₂H on pyridin-3-yl / phenyl (positions 3,4,5, R) ketoxime structure

| Ex. No. | m | R | $R_f$ value* |
|---|---|---|---|
| II | 4 | 3-NH—SO₂—C₆H₄—F (para) | 0.36 |
| III | 4 | 3-NH—SO₂—C₆H₃(Cl)(Cl) (2,6-diCl) | 0.35 |
| IV | 4 | 3-NH—SO₂—C₆H₄—OCF₃ | 0.35 |
| V | 4 | 3-NH—SO₂—C₆H₄—CF₃ | 0.30 |
| VI | 4 | 3-NH—SO₂—C₆H₄—O—Ph | 0.36 |
| VII | 4 | 3-NH—SO₂—C₆H₄—CN | 0.31 |
| VIII | 4 | 3-NH—SO₂—C₆H₄—C(CH₃)₃ | 0.37 |
| IX | 4 | 2-NH—SO₂—C₆H₄—Cl | 0.39 |
| X | 4 | 4-NH—SO₂—C₆H₄—Cl | 0.30 |
| XI | 3 | 3-NH—SO₂—C₆H₄—Cl | 0.37 |
| XII | 5 | 3-NH—SO₂—C₆H₄—Cl | 0.36 |

*CH₂Cl₂/MeOH = 10:1

EXAMPLE XIII (E/Z)-7-[[[3-Pyridinyl-3-(4-chlorophenylsulphonamido)phenyl]methylene]iminooxy]heptane-carboxylic acid

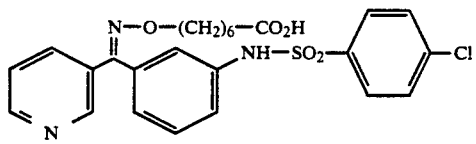

3.25 g (8.4 mmol) of the oxime from Example 11 are dissolved in 6.3 ml of abs. THF and the mixture is added dropwise with exclusion of air to a suspension of 0.55 g (18.3 mmol) of sodiumhydride (80% strength in mineral oil) in 6.3 ml of abs. THF. A further 20 ml of abs. THF are added for better stirrability. The mixture is heated to reflux for 1 h and 2.19 g (9.2 mmol) of ethyl 7-bromoheptanecarboxylate are then added dropwise. The mixture is then refluxed for 21 h, and the solid is filtered off and washed well with THF. The THF phase is evaporated, the residue is taken up in 30 ml of methylene chloride and the solution is washed with 30 ml of 10% strength NaOH solution and 30 ml of saturated NaCl solution. After drying over Na₂SO₄, it is evaporated and the residue is chromatographed on silica gel using CH₂Cl₂/ acetone 20:1 as the eluent. The fractions containing the product as the ethyl ester are combined and evaporated. For hydrolysis, the ester is dissolved in 15 ml of methanol and 8.4 ml (10 mmol) of 1 N NaOH are added. The mixture is stirred at room temperature for 3 h, then heated to reflux for 30 min. The methanol is stripped off in a water-jet vacuum, 20 ml of water are added and the mixture is extracted using 20 ml of CH₂Cl₂. The aqueous phase is adjusted to pH 5 with 1 N HCl and extracted 3 times with 30 ml of THF each time, to which some ethyl acetate is added for better phase separation. The THF phase is dried over Na₂SO₄ and evaporated. After drying in a high vacuum the clean product is obtained.

Yield: 0.51 g (11.8% of theory)
$R_f$=0.28 (CH₂Cl₂/MeOH 10:1)

EXAMPLE XIV (E/Z)-5-[[[(3-Pyridinyl)-3-(4-chlorophenyl-sulphonamidomethyl)phenyl]methylene]iminooxy]pentanecarboxylic acid

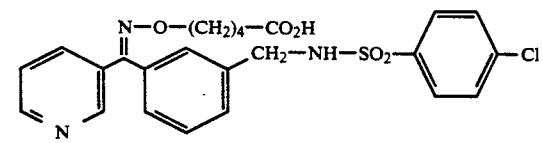

The ketone from Example 15 is reacted with 5-aminooxypentanecarboxylic acid hydrochloride analogously to Example I.

Yield: 72%
$R_f$=0.36 (CH₂Cl₂/CH:OH 10:1)

EXAMPLE XV (E/Z)-7-[3-[4-Chlorophenylsulphonamido]phenyl]-7-(3-pyridinyl)-6-heptenecarboxylic acid

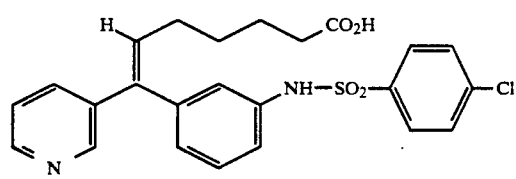

0.95 g (3.2 mmol) of the amine from Example 16 and 0.85 g (4.1 mmol) of 4-chlorobenzenesulphonyl chloride are heated to reflux for 2 h in 6.4 ml of pyridine. After cooling, the mixture is poured into 40 ml of ice-cold 6 N HCl and the aqueous phase is decanted off from the oily precipitate. The oily precipitate is dissolved in 40 ml of methanol and the solution is then evaporated. The residue is chromatographed on silica gel using $CH_2Cl_2$/MeOH 10:1 as the eluent.

Yield: 0.8 g (53.1.% of theory)
$R_f$ = 0.7 ($CH_2Cl_2$/MeOH 10:1)

The sulphonamides summarised in Table 4 were prepared in an analogous manner:

TABLE 4

| Ex. No. | Position | m | n | X | $R_f$* |
|---|---|---|---|---|---|
| XVI | 3 | 3 | 0 | —⌬—Cl | 0.59 |
| XVII | 3 | 3 | 0 | —⌬—F | 0.55 |
| XVIII | 3 | 4 | 0 | —⌬ | 0.54 |
| XIX | 3 | 4 | 0 | —⌬—$CH_3$ | 0.63 |
| XX | 3 | 5 | 0 | —⌬—Cl | 0.62 |
| XXI | 3 | 5 | 0 | —⌬—N | 0.27 |
| XXII | 3 | 6 | 0 | —⌬—Cl | 0.62 |
| XXIII | 3 | 6 | 0 | —⌬—N | 0.28 |
| XXIV | 4 | 4 | 0 | —⌬—Cl | 0.64 |
| XXV | 3 | 4 | 1 | —⌬—Cl | 0.66 |

*$CH_2Cl_2$/MeOH = 10:1

EXAMPLE XXVI 7-(3-[4-Chlorophenylsulphonamido]phenyl)-7-(3-pyridinyl)heptenecarboxylic acid

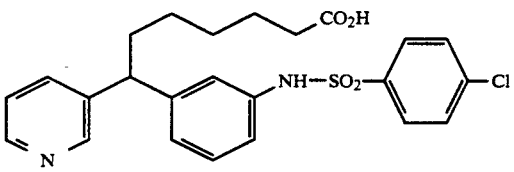

2.6 g (5.5 mmol) of the heptenecarboxylic acid from Example XV are hydrogenated with hydrogen at normal pressure and at room temperature in the presence of 0.51 ml (5.5 mmol) of 70% perchloric acid in 16.5 ml of abs. ethanol using 0.69 g of Pd-C/10% strength as a catalyst. After 6 h, the reaction was complete on TLC (starting substance can be stained rapidly using 0.5% strength $KMnO_4$ solution). The catalyst is filtered off, 30 ml of saturated $NaHCO_3$ solution are added and the mixture is then extracted 3 times using ethyl acetate. The combined ethyl acetate phases are washed with saturated NaCl solution, dried over $Na_2SO_4$ and evaporated. As the heptenecarboxylic acid is formed on hydrogenation of the ethyl ester, the residue is directly hydrolysed. To do this, the residue is dissolved in 10 ml of methanol, 2.4 ml (5.8 mmol) of 2 N NaOH solution are added and the mixture is refluxed for 30 min. The solution is evaporated, 10 ml of $H_2O$ are added and the mixture is washed twice with $CH_2Cl_2$. The aqueous phase is then adjusted to pH 5.5 using 10% strength HCl and shaken 3 times with ethyl acetate. The combined organic phases are dried over $Na_2SO_4$ and evaporated. The residue is chromatographed on silica gel using $CH_2Cl_2$/MeOH as the eluent.

Yield: 1.38 g (53.1% of theory)
$R_f = 0.3$ (CH$_2$Cl$_2$/MeOH 10:1)

What is claimed is:

1. An aryl sulfonamide derivative according to the formula (I)

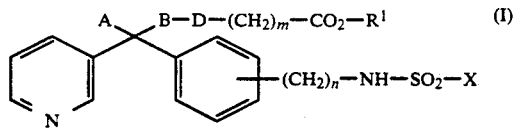

in which
A—represents hydrogen,
B—represents the —CH$_2$— group, or
A and B together represent a radical of the formula =CN— or =N—, D—represents the —CH$_2$— group or in the case in which B denotes the radical of the formula =N—, then D represents oxygen,
m—represents a number, 1, 2, 3, 4, 5, 6, 7, 8, 9 or 10,
$R^1$—represents hydrogen or straight-chain or branched alkyl having up to 8 carbon atoms, or phenyl,
n—represents a number 0 to 4,
X—represents aryl having 6 to 10 carbon atoms which is optionally monosubstituted to trisubstituted by identical or different substituents from the series comprising halogen, cyano, phenoxy, trifluoromethoxy and straight-chain or branched alkyl having up to 8 carbon atoms, which, in turn, can be monosubstituted to trisubstituted by identical or different halogen substituents,
or a physiologically acceptable salt thereof.

2. A phenylsulphonamide substituted pyridinealkene- and aminooxyalkanecarboxylic acid derivative or salt thereof according to claim 1, in which
A—represents hydrogen,
B—represents the —CH$_2$— group, or
A and B together represent a radical of the formula =CH— or =N—, D—represents the —CH$_2$— group or in the case in which B with A denotes the radical of the formula =N—, then D represents oxygen,
m—represents a number 1, 2, 3, 4, 5, 6, 7 or 8,
$R^1$—represents hydrogen or straight-chain or branched alkyl having up to 6 carbon atoms,
n—represents a number 0 or 1,
X—represents phenyl which is optionally monosubstituted to trisubstituted by identical or different substituents from the series comprising fluorine, chlorine, bromine, cyano, phenoxy, trifluoromethyl, trifluoromethoxy and straight-chain or branched alkyl having up to 6 carbon atoms.

3. A phenylsulphonamide substituted pyridinealkene- and aminooxyalkanecarboxylic acid derivative or salt thereof according to claim 1, in which
A—represents hydrogen,
B—represents the —CH$_2$— group, or
A and B together represent a radical of the formula
=CH— or =N—,
D—represents the —CH$_2$— group or in the case in which B with A denotes the radical of the formula =N—, then D represents oxygen, m—represents a number 1, 2, 3, 4, 5 or 6,
$R^1$—represents hydrogen or straight-chain or branched alkyl having up to 4 carbon atoms,
n—represents a number 0 or 1,
X—represents phenyl which is optionally monosubstituted to trisubstituted by identical or different substituents from the series comprising fluorine, chlorine, cyano, phenoxy, trifluoromethyl, trifluoromethoxy and straight-chain or branched alkyl having up to 4 carbon atoms.

4. A compound according to claim 1, wherein such compound is (E/Z)-5-[[[3-pyridinyl-3-(4-chlorophenylsulphonamido)phenyl]methylene]iminooxy]pentane carboxylic acid of the formula

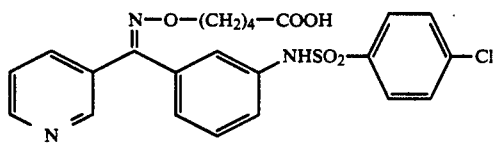

or a salt thereof.

5. A compound according to claim 1, wherein such compound is (E/Z)-5-[[[3-pyridinyl-3-(4-fluorophenylsulphonamido)phenyl]methylene]iminooxy]pentane carboxylic acid of the formula

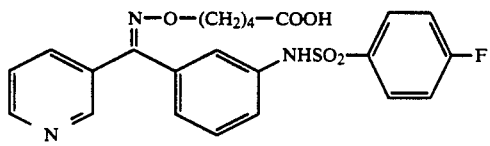

or a salt thereof.

6. A compound according to claim 1, wherein such compound is (E/Z)-7-[3-(4-chlorophenylsulphonamido)- phenyl]-7-(3-pyridinyl)-6-heptene carboxylic acid of the formula

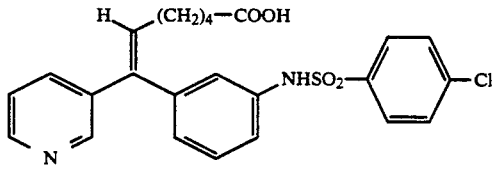

or a salt thereof.

7. A compound according to claim wherein such compound is (E/Z)-7-[4-(4-chlorophenylsulphonamido)phenyl]-7-(3-pyridinyl)-6-heptene carboxylic acid of the formula

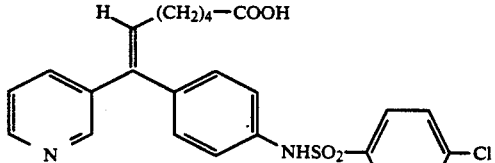

or a salt thereof.

8. A compound according to claim wherein such compound is (E/Z)-7-[3-(4-chlorophenylsulphonamidomethyl)phenyl]-7-(3-pyridinyl)-6-heptene carboxylic acid of the formula

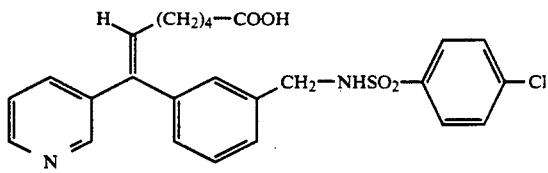

or a salt thereof.

9. A pharmaceutical composition comprising an effective amount of a compound according to the formula I of claim 1 in combination with a pharmaceutical excipient.

10. A method of inhibiting platelet aggregation by suppressing thromboxane $A_2$ in a patient in need thereof, which comprises administering to said patient, an effective amount of compound according to the formula I of claim one.

11. The method according to claim 13, wherein said compound represents a member selected from the group consisting of (E/Z)-5-[[[3-pyridinyl-3-(4-chlorophenyl-sulphonamido) phenyl]methylene]imino-oxy]pentane carboxylic acid, (E/Z)-5-[[[3-pyridinyl-3-(4-fluorophenyl-sulphonamido) phenyl]methylene]imino-oxy]pentane carboxylic acids, (E/Z)-7-[3-(4-chlorophenyl-sulphonamido)phenyl]-7-(3-pyridinyl)-6-heptene carboxylic acids, (E/Z)-7-[4-(4-chlorophenylsulphonamido)phenyl]-7-(3-pyridinyl)-6-heptene carboxylic acid, (E/Z)-7-[3-(4-chlorophenylsulphonamido-methyl)-phenyl]-7-(3-pyridinyl)-6-heptene carboxylic acid, or a salt thereof.

* * * * *

UNITED STATES PATENT AND TRADEMARK OFFICE
CERTIFICATE OF CORRECTION

PATENT NO. : 5,155,121

DATED : October 13, 1992

INVENTOR(S) : Niewohner, et al.

It is certified that error appears in the above-identified patent and that said Letters Patent is hereby corrected as shown below:

Col. 20, line 52   After " claim " insert -- 1 --.

Col. 20, claim 8 line 1   After " claim " insert -- 1 --.

Col. 22, line 3   Delete " claim 13 " and substitute -- claim 10 --.

Signed and Sealed this

Twenty-ninth Day of March, 1994

Attest:

BRUCE LEHMAN

*Attesting Officer*        *Commissioner of Patents and Trademarks*